United States Patent [19]

Powell

[11] 4,431,825

[45] Feb. 14, 1984

[54] PREPARATION OF ALKENYL SUCCINIC ANHYDRIDES

[75] Inventor: Justin C. Powell, Fairfax, Va.

[73] Assignee: Texaco Inc., White Plains, N.Y.

[21] Appl. No.: 367,822

[22] Filed: Apr. 12, 1982

[51] Int. Cl.³ .......................................... C07D 307/60
[52] U.S. Cl. .................................... 549/255; 549/254
[58] Field of Search ................................ 549/255, 254

[56] References Cited

U.S. PATENT DOCUMENTS 2,297,039 9/1942 van Melsen ......................... 549/255
3,954,812 5/1976 Puskas et al. ....................... 549/255

FOREIGN PATENT DOCUMENTS

F 10267 9/1956 Fed. Rep. of Germany ...... 549/255
1396097 5/1975 United Kingdom ................ 549/255

OTHER PUBLICATIONS

Ellis, The Chem. of Synthetic Resins–vol. 1, Reinhold Publ. (1935), pp. 164–168.

*Primary Examiner*—Richard Raymond
*Assistant Examiner*—Bernard Dentz
*Attorney, Agent, or Firm*—Carl G. Ries; Robert A. Kulason; Carl G. Seutter

[57] ABSTRACT

Products typified by alkenyl-substituted succinic acid anhydrides are prepared by reacting olefin oligomers with anhydrides of unsaturated aliphatic polycarboxylic acids in the presence of ferric chloride, ferric bromide, stannic chloride, or phosphoric acid $H_3PO_4$ as catalyst.

13 Claims, No Drawings

PREPARATION OF ALKENYL SUCCINIC ANHYDRIDES

FIELD OF THE INVENTION

This invention relates to the preparation of alkenyl-substituted polycarboxylic acid anhydrides. More particularly it relates to preparation of such products in the presence of a catalyst system.

BACKGROUND OF THE INVENTION

Alkenyl succinic acid anhydride type compounds may be typically prepared by the reaction of a polyisobutene and maleic acid anhydride, in the presence of catalyst such as 1,3-dibromo-5,5-dialkyl hydantoin. It is found however that the reaction mixture contains undesirable sludge in amount which may be as high as 6–7 wt%.

It is an object of this invention to provide a process for preparing alkenyl-substituted succinic acid anhydrides in the presence of a catalyst which permits operation characterized by formation of increased amounts of product with decreased amounts of sludge. Other objects will be apparent to those skilled in the art.

STATEMENT OF THE INVENTION

In accordance with certain of its aspects, the method of this invention may comprise reacting at 150° C.–300° C. in the presence of a catalyst selected from the group consisting of ferric chloride, ferric bromide, stannic chloride, and phosphoric acid $H_3PO_4$ (i) an olefin oligomer reactant of molecular weight $\overline{M}_n$ of 250–30,000; and (ii) an anhydride of an unsaturated aliphatic polycarboxylic acid in amount of 0.5–5 moles per mole of olefin oligomer, thereby forming product alkenyl-substituted polycarboxylic acid anhydride; and recovering said product alkenyl-substituted polycarboxylic acid anhydride.

DESCRIPTION OF THE INVENTION

The unsaturated aliphatic polycarboxylic, preferably dicarboxylic acid anhydrides which may be employed to form the desired alkenyl-substituted dicarboxylic acid anhydrides in practice of this invention may be intramolecular anhydrides typified by the following:

TABLE

| maleic | anhydride |
| citraconic | anhydride |
| itaconic | anhydride |
| ethylmaleic | anhydride |
| halo(eg chloro)maleic | anhydride, etc. |

The preferred anhydride may be maleic acid anhydride.

The olefin oligomer, or polyolefin, reactant which may be employed may typically be an oligomer of a $C_2$–$C_8$ olefin having a molecular weight $\overline{M}_n$ of about 250–30,000, more commonly about 300–3000, say 1000–1500. The preferred oligomers are the polyisobutylenes, more preferably polyisobutylene of $\overline{M}_n$ of 250–5000, preferably 300–3000, say about 1300.

The polybutenes which may be employed may include those polymers obtained by polymerizing refinery streams containing eg isobutylenes, cis-butene-2, trans-butene-2, and butene-1. Polymerization of such streams, typically by use of a Friedel-Crafts catalyst, permits attainment of a polyisobutylene of $\overline{M}_n$ of 250–5000, preferably 500–2000, say 700–1500, typically 1050–1400, and a viscosity of 4–5500 centistokes at 100° C. Molecular weight $\overline{M}_n$ may be determined by ASTM D-2503 method.

Reaction between the polyolefin and the typical unsaturated aliphatic dicarboxylic acid anhydride to form the desired product alkenyl-substituted aliphatic dicarboxylic acid anhydride may be carried out at 150° C.–300° C. preferably about 210° C.–245° C., say about 245° C. for 2–10, preferably 4–10, say 6 hours at autogenous pressure in batch operation or at 150° C.–300° C., preferably 210° C.–245° C., say about 245° C. for 1–3 hours in a continuous process.

It is a feature of the novel process of this invention that it be carried out in the presence of a catalyst selected from the group consisting of ferric chloride, ferric bromide, stannic chloride, and phosphoric acid $H_3PO_4$.

It is preferred that these compounds be substantially in anhydrous form. In the case of ferric chloride it may be desirable to use either hydrous ferric chloride such as the hexahydrate $FeCl_3.6H_2O$ or more preferably the anhydrous $FeCl_3$. The anhydrous form of stannic chloride ($SnCl_4$) is preferred. In the case of the phosphoric acid, it may be desirable to use 85 w % $H_3PO_4$, anhydrous phosphoric acid, polyphosphoric acid, or phosphorus pentoxide $P_2O_5$.

In typical operation, the catalyst may be added to the reaction mixture in amount up to about 5 w % (based upon olefin charged) although it will be preferably employed in amount less than about 2 w %. Commonly the catalyst may be present in amount of 0.5 w %–2 w %, say about 1 w %.

Thus there may be added to the reaction medium in which the alkenyl-substituted polycarboxylic acid anhydride is to be prepared, the following parts of the several components:

TABLE

| Component | Broad | Preferred | Typical |
|---|---|---|---|
| Olefin | 250–30,000 | 800–3000 | 1290 |
| Anhydride | 50–500 | 50–200 | 107.8 |
| Catalyst | 0.1–50 | 0.2–25 | 11.6 |

Reaction may be carried out at the following conditions:

TABLE

| Condition | Broad | Preferred | Typical |
|---|---|---|---|
| Temp. °C. | 150–300 | 210–280 | 245 |
| Pressure psig (Max) | 15–500 | 50–200 | 90 |
| Mole ratio Anhydride to olefin | 0.2–5 | 0.5–2 | 1.1 |

When the reaction is carried out in batch operation, the time of reaction may be 2–10 hours, preferably 4–10 hours, say 6 hours. When the reaction is carried out continuously, the time may be 4–10 hours, preferably 1–3 hours, say 2 hours.

During the course of the reaction, the olefin oligomer, typically polyisobutylene, and the anhydride typically maleic acid anhydride, react to yield product alkenyl-substituted polycarboxylic acid anhydride, typically polyisobutenyl succinic acid anhydride. At the conclusion of the reaction, excess unreacted charge aliphatic polycarboxylic acid anhydride is stripped off and condensed. The crude product is then filtered to separate sludge therefrom.

It is a feature of the process of this invention that use of the novel catalyst systems permits attainment of product containing lower content of sludge. Sludge content is generally found to be less than about 1.2 w % (based on total weight of reactants). Sludge content of 0.6-1.1 w % is typically found; and under preferred conditions of operation, the sludge content may be only 0.7-0.9 w %.

The yield of desired product, expressed as percent DPIB, i.e. derivatized polyisobutylene, (calculated as 100% minus % polyisobutylene in hexane eluate) may in typical operation be maintained consistently above about 60%, typically as high as 66-67%.

In one pair of examples conducted under comparable conditions, the sludge was reduced from eg 1.1 w % to 0.62 w %, (a 44% improvement) while the yield of desired derivatized polyisobutylene was increased.

It will be seen that the use of the process of this invention permits attainment of several advantages:
(i) attainment of increased yield of desired product;
(ii) attainment of reaction mixture having decreased sludge content.

The product, typically alkenyl-substituted succinic acid anhydride, prepared by the process of this invention may be used as additive to a hydrocarbon such as a motor fuel (to provide increased rust inhibition and carburetor detergency) or a lubricating oil (to provide rust inhibition) etc. They may also be used to prepare ester, imide, or amide derivatives which are widely employed as additives in motor fuels and lubricants.

DESCRIPTION OF PREFERRED EMBODIMENTS

Practice of the process of this invention will be apparent to those skilled in the art from the following wherein, as elsewhere in this specification, all parts are parts by weight unless otherwise stated.

EXAMPLE I

In this example which shows a preferred embodiment for carrying out the process of this invention, there is added to a reaction vessel 1290 parts of Indopol H-300 brand of polyisobutylene ($\bar{M}_n$ of 1290), 107.8 parts of maleic acid anhydride, and 11.6 parts of anhydrous ferric chloride, this corresponds to a catalyst concentration of 0.9 w % based on charge polyisobutylene. The reaction vessel is sealed and the mixture heated to 245° C. at autogenous pressure of 36-73 psig for 6 hours with agitation. At the end of the reaction time, the mixture is found to have changed from a light straw color to a dark brown color. During the course of the reaction, there is formed product polyisobutenyl succinic acid anhydride. Analysis reveals a sludge content of only 0.77 w %, a % DPIB of 66.4, and a Sap No. of 56. These results are significantly superior to a run without catalyst—see Example XXI in which a Sap. No. of about 44, a % DPIB of 57.1, and a % sludge of 1.1 are obtained.

EXAMPLES II–VIII

In the series of Examples in the following Table I the procedure of Example I was carried out except that the catalyst, catalyst concentration, the mole ratio of maleic acid anhydride to polyisobutylene, the temperature of operation, and the pressure were varied. The duration of the run and temperature were 10 hours at 216° C. in Example II and 6 hours at 245° C. in Examples III–VIII.

Tables I–III list the following inter alia:
(i) Concentration as parts of catalyst per 10,000 parts of Indopol H-300 polyisobutylene charged.
(ii) Mole ratio of maleic acid anhydride to Indopol H-300 polyisobutylene;
(iii) Pressure psig—the range of autogeneous pressure at the reaction temperature.
(iv) Sap No.—The saponification number determined by ASTM Method D-94.
(v) % DPIB—Derivatized polyisobutylene determined as 100% minus the percent of unreacted polyisobutylene eluted by hexane.
(vi) Sludge—The weight % of sludge based upon total reactants charged.

TABLE I

| Example | Additive | Conc. | Mole Ratio | Pressure psig | Sap No. | % DPIB | Sludge wt % |
|---|---|---|---|---|---|---|---|
| II | FeCl$_3$ | 25 | 2.0 | 50–250 | 31 | 39.3 | 9.8 |
| III | FeCl$_3$ | 2 | 1.1 | 35–72 | 54 | 65.5 | 0.88 |
| IV | FeCl$_3$.6H$_2$O | 1 | 1.1 | 38–70 | 52 | 63.9 | 0.62 |
| V | FeCl$_2$ | 1 | 1.1 | 40–121 | 50 | 58.1 | 1.5 |
| VI | FeBr$_3$ | 1 | 1.1 | 39–78 | 53 | 67.5 | 1.1 |
| VII | FeCl$_3$.6H$_2$O | 1 | 2.0 | 43–220 | 65 | 75.0 | 3.9 |
| VIII | FeCl$_3$.6H$_2$O | 1.5 | 1.1 | 37–59 | 51 | 63.5 | 0.68 |

From the above, it will be apparent that when the mole ratio of maleic acid anhydride to polyisobutylene (Example II and VII) is undesirably above the preferred upper limit, the sludge production is undesirably high. It is apparent (Example V) that use of ferrous chloride FeCl$_2$ gives a product undesirably containing 1.5 w % sludge. The preferred Example I gives a sludge content of only 0.77 w % together with a desirably high % DPIB (66.4%) and a desirably high Sap. No. (56).

EXAMPLES IX–XIX

In this series of Examples, a series of runs is carried out in which anhydrous ferric chloride FeCl$_3$(FCA) is used as catalyst. The concentration of catalyst and the conditions of operation are varied as indicated in Table II. The entries are as in Table I except that the pressure in psig is set forth as (i) the maximum autogenous pressure during the reaction and also (ii) as X.S.—i.e. (i) the pressure of the reaction vessel during reaction and (ii) after the reaction vessel has been cooled to room temperature of about 25° C.

TABLE II

| Example | FCA Conc. | Mole Ratio | Temp. °C. | Time hr | Pressure Max. | Pressure X.S. | Sludge Wt % | Sap No. | % DPIB |
|---|---|---|---|---|---|---|---|---|---|
| IX | 0.90 | 1.1 | 245 | 6.0 | 73 | 31 | 0.77 | 57.4 | 66.4 |

TABLE II-continued

| Example | FCA Conc. | Mole Ratio | Temp. °C. | Time hr | Pressure Max. | Pressure X.S. | Sludge Wt % | Sap No. | % DPIB |
|---|---|---|---|---|---|---|---|---|---|
| X | 1.40 | 1.4 | 255 | 8.0 | 159 | 71 | 1.4 | 64.1 | 73.1 |
| XI | 1.40 | 1.4 | 235 | 4.0 | 50 | 20 | 0.94 | 47.9 | 58.6 |
| XII | 0.40 | 0.8 | 235 | 4.0 | 39 | 0 | 0.59 | 34.4 | 46.7 |
| XIII | 0.40 | 1.4 | 255 | 4.0 | 135 | 58 | 1.8 | 58.9 | 65.9 |
| XIV | 0.90 | 1.1 | 245 | 6.0 | 65 | 23 | 0.74 | 51.6 | 61.7 |
| XV | 1.40 | 0.8 | 235 | 8.0 | 40 | 10 | 0.53 | 40.5 | 52.9 |
| XVI | 1.40 | 0.8 | 255 | 4.0 | 45 | 10 | 0.31 | 44.5 | 54.7 |
| XVII | 0.40 | 0.8 | 255 | 8.0 | 81 | 32 | 0.50 | 42.9 | 51.2 |
| XVIII | 0.40 | 1.4 | 235 | 8.0 | 119 | 50 | 1.43 | 53.0 | 63.4 |
| XIX | 0.90 | 1.1 | 245 | 6.0 | 76 | 31 | 0.92 | 54.1 | 63.1 |

From the above, it is apparent that the sludge contents increase as a result of three factors: high mole ratios, extended reaction time, and elevated temperature. It may be noted that Examples X and XIII, in which all these factors are large, result in undesirably high sludge content. In Example XVIII where the mole ratio and time are high, and the temperature is only 235° C., a high sludge content is noted.

Example IX is shows the best mode known to me of practicing the process of this invention giving a low sludge content (0.88%) and a high yield 66.4%. The conditions of 0.9, (i) mole ratio of 1.1, (ii) temperature of 245° C., and (iii) time of 6 hours result in excellent conversion to desired product and low sludge formation with use of only a modest excess of maleic acid anhydride.

TABLE III

| Example | Catalyst I.D. | Catalyst Conc. | Pressure, psig Max. | Pressure, psig XS | Sap No. | % DPIB | Sludge Wt % |
|---|---|---|---|---|---|---|---|
| XX* | Dibromantin | 1 | 55–71 | 20–30 | 50–59 | 67.3–68.5 | 0.62–1.2 |
| XXI* | None | 0 | 95 | 25 | 41, 47 | 57.1 | 1.1 |
| XXII | SnCl$_4$ (anh.) | 1.0 | 111 | 48 | 50, 52 | 64.3 | 0.92 |
| XXIII | H$_3$PO$_4$ (85%) | 1.0 | 85 | 36 | 53 | 63.8 | 1.1 |
| XXIV* | ZnCl$_2$ | 1.0 | 145 | 65 | 47, 49 | 59.7 | 1.7 |
| XXV* | AlCl$_3$ (anh.) | 1.0 | 100 | 42 | 52, 52 | 62.7 | 1.5 |
| XXVI* | Ce(HSO$_4$)$_4$ | 1.0 | 110 | 49 | 49, 52 | 58.4 | 1.5 |

*control examples

From the above Table, it will be apparent for example that the results of the Experimental Example XXIII show that practice of the process of this invention using 85% H$_3$PO$_4$ permits attainment of desirable results characterized by sludge content (1.1 w %), and high Saponification Number (53). This result is comparable to the result attained in control Example XX using dibromantin (i.e. 1,3-dibromo-5,5-dimethyl hydantoin) and is superior to the control of Example XXII using no catalyst in that a higher conversion to alkenyl succinic acid anhydride is obtained as shown by the Sap. No. of 63.8.

The process of Example XXII, using tin tetrachloride SnCl$_4$ was satisfactory in that it provided a low sludge content (0.92%) and a high Sap. No. (64.3).

Control examples XX*–XXI* and XXIV*–XXVI* show generally poor results characterized by lower Sap. No. or higher sludge content, or both.

Although this invention has been illustrated by reference to specific embodiments, it will be apparent to those skilled in the art that various changes and modifications may be made which clearly fall within the scope of this invention.

I claim:

1. The method of preparing a product alkenyl-substituted polycarboxylic acid anhydride which comprises
   reacting at 150° C.–300° C. in the presence of a catalyst selected from the group consisting of ferric chloride, ferric bromide, and stannic chloride,
   (i) an olefin oligomer reactant of molecular weight $\overline{M}_n$ of 250–30,000; and
   (ii) an anhydride of an unsaturated aliphatic polycarboxylic acid in amount of 0.5–5 moles per mole of olefin oligomer, thereby forming product alkenyl-substituted polycarboxylic acid anhydride; and
   recovering said product alkenyl-substituted polycarboxylic acid anhydride.

2. The method of preparing a product alkenyl-substituted polycarboxylic acid anhydride as claimed in claim 1 wherein said olefin oligomer is polyisobutylene.

3. The method of preparing a product alkenyl-substituted polycarboxylic acid anhydride as claimed in claim 1 wherein said olefin oligomer is polyisobutylene of molecular weight $\overline{M}_n$ of 250–5,000.

4. The method of preparing a product alkenyl-substituted polycarboxylic acid anhydride as claimed in claim 1 wherein said olefin oligomer is polyisobutylene of molecular weight $\overline{M}_n$ of 300–3000.

5. The method of preparing a product alkenyl-substituted polycarboxylic acid anhydride as claimed in claim 1 wherein said anhydride of an unsaturated aliphatic polycarboxylic acid is maleic acid anhydride.

6. The method of preparing a product alkenyl-substituted polycarboxylic acid anhydride as claimed in claim 1 wherein the mole ratio of polycarboxylic acid anhydride to olefin is 0.5–2.

7. The method of preparing a product alkenyl-substituted polycarboxylic acid anhydride as claimed in claim 1 wherein the mole ratio of polycarboxylic acid anhydride to olefin is 0.8–1.5.

8. The method of preparing a product alkenyl-substituted polycarboxylic acid anhydride as claimed in claim 1 wherein said catalyst is anhydrous ferric chloride FeCl$_3$.

9. The method of preparing a product alkenyl-substituted polycarboxylic acid anhydride as claimed in claim 1 wherein said catalyst is hydrous ferric chloride.

10. The method of preparing a product alkenyl-substituted polycarboxylic acid anhydride as claimed in claim 1 wherein said catalyst is ferric bromide.

11. The method of preparing a product alkenyl-substituted polycarboxylic acid anhydride as claimed in claim 1 wherein said catalyst is stannic chloride.

12. The method of preparing a product alkenyl-substituted polycarboxylic acid anhydride as claimed in claim 1 wherein said catalyst is present in amount of 0.5–5 w % based on olefin charged.

13. The method of preparing a product alkenyl-substituted succinic acid anhydride which comprises reacting at 150° C.–300° C., in the presence of ferric chloride catalyst, (i) polyisobutylene of molecular weight of 250–5000 and (ii) maleic acid anhydride in amount of 0.5–5 moles per mole of polyisobutylene thereby forming product polyisobutenyl succinic acid anhydride; and recovering said product polyisobutenyl succinic acid anhydride.

* * * * *